Aug 6, 1974 T. H. JOHNSON ET AL Plant Pat. 3,585
ROSE PLANT
Filed Feb. 20, 1973
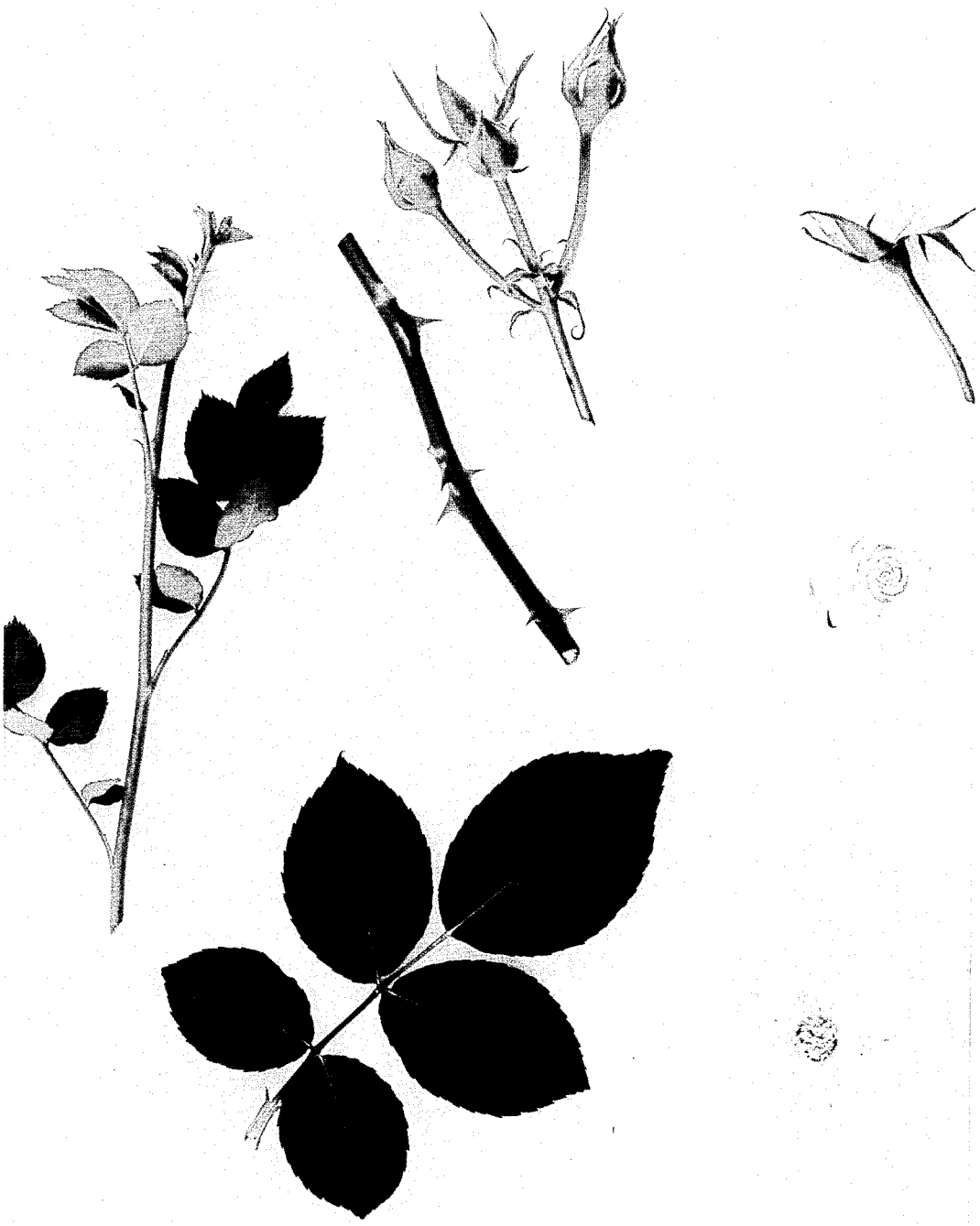

United States Patent Office

Plant Pat. 3,585
Patented Aug. 6, 1974

3,585
ROSE PLANT

Theodore H. Johnson, Hadley, Mass., and William A. Warriner, Tustin, Calif., assignors to Jackson & Perkins Company, Medford, Oreg.

Filed Feb. 20, 1973, Ser. No. 333,747
Int. Cl. A01h *5/00*
U.S. Cl. Plt.—26 1 Claim

The present invention relates to a new and distinct variety of rose plant of the floribunda class which was discovered in a commercial greenhouse bed of the variety "Seventeen," U.S. Plant Pat. 1,765. This discovery was made by Theodore H. Johnson in a greenhouse in Hadley, Mass. William A. Warriner propagated the sport at Wasco, Calif. and grew the plants in a greenhouse at Irvine, Calif.

This new mutation was recognized as being similar to the variety "Seventeen," but being different in several respects as evidenced by the following unique combination of characteristics which are outstanding in the new variety and which distinguish it from "Seventeen" as well as from all other varieties of which we are aware:

1. Foliage is slightly larger, and generally, under good growing conditions, slightly darker green than the variety "Seventeen."
2. Bud and flower color are a clear Venetian pink (Wilson's), fading only slightly after open three or four days.

Asexual reproduction of this new variety by budding, as performed at Wasco, Calif., shows that the foregoing characteristics and distinctions come true to form and are established and transmitted through succeeding propagations.

The accompanying drawing shows typical specimens of the vegetative growth and flowers of this new variety in different stages of development, depicted in color as nearly true as it is reasonably possible to make the same in a color illustration of this character.

The following is a detailed description of our new rose variety with color terminology in accordance with *Wilson's Horticultural Color Chart,* except where ordinary dictionary significance of color is indicated.

Parentage:
*Sport.*—Of variety "Seventeen," U.S. Pl. Pat. 1,765.
Classification:
*Botanic.*—*Rosa hybrid.*
*Commercial.*—Floribunda.

FLOWER

Observations were made at Tustin, Calif. in early August of plants in greenhouse.

Blooming habit: Recurrent—continuous.
Bud:
*Size.*—One inch when petals start to unfurl.
*Form.*—Blunt top.
*Color.*—When sepals first divide Venetian pink (420/2). When half blown; inside of petals—Venetian pink (420/2), reverse of petals Venetian pink (420/2).
*Sepals.*—Color: Outer surface—Scheeles green (860/3). Inner surface—Scheeles green (860/3) lightly covered with white tomentum. Three appendaged sepals normally appendaged. Two unappendaged sepals smooth edged.
*Receptacle.*—Color: Scheeles green (860/3). Shape: Funnel. Size: Large and broad relative to flower size. Surface: Smooth.
*Peduncle.*—Length: Medium. Surface: Prickly; prickles are glandular. Color: Light green. Strength: Stiff and erect.

*Opening.*—Petals fold out with very little curling.
Bloom:
*Size.*—Average size when fully expanded is 2½ to 3 inches.
*Borne.*—In clusters.
*Stems.*—Medium.
*Form.*—When first open, high center. Permanence—outer petal edges slightly curl.
*Petalage.*—Number of petals under normal conditions approximately 35.
*Color.*—Center of flower: Upper side of petals slightly lighter than Venetian pink (420/3). Reverse side of petals same. Outer petals: Upper side of petals near white with light overlay of color lighter than Venetian pink (420/3). Reverse of petals same. Base of petals: Small area near Uranium green (63/3). General tonality from a distance, lighter than Venetian pink (420/3). No variegations.
*Discoloration.*—General tonality at end of first day lighter than Venetian pink (420/3). By third day lightens a little. When petals fall they are only slightly tinted with Venetian pink.
*Fragrance.*—Slight.
Petals:
*Texture.*—Leathery.
*Surface.*—Inside—satiny. Reverse—satiny.
*Shape.*—Round.
*Form.*—Tips slightly recurved.
*Arrangement.*—Imbricated.
*Petaloids in center.*—Few.
*Persistence.*—Drop off cleanly.
*Lastingness.*—On the plant—very long. As cut flower—very long.
Reproductive parts:
*Stamens, Anthers.*—Large, many. Color—yellow. Arrangement—regular around styles.
*Stamens, filaments (threads).*—Medium and short. Color—Uranium green (63/3).
*Pollen.*—Golden yellow.
*Styles.*—Loosely separated, of uneven lengths.
*Stigmas.*—Color—yellow.

PLANT

Form: Bush.
Growth: Very vigorous.
Foliage: Number of leaflets on normal mid-stem leaves 5.
*Size.*—Large.
*Quantity.*—Normal.
*Color.*—New foliage: Slightly lighter than Garnet brown (00918/3). Old foliage: Near Parsley green (00962/1) upper side; lower side—Willow green (000862).
Leaflets:
*Shape.*—Oval, pointed.
*Texture.*—Leathery. Under side smooth. Ribs and veins ordinary.
*Edge.*—Serrated and slightly undulated.
*Serration.*—Single, small sized.
*Petiole (rachis).*—Color—green. Underside few prickles.
*Stipules.*—Short and smooth.
*Disease resistance.*—Slightly susceptible to mildew under normal growing conditions at Tustin, Calif.
Wood:
*New Wood.*—Color—light green. Bark—smooth.
*Old Wood.*—Color—green. Bark—smooth.
Prickles:
*Quantity.*—On main stalks—few. On laterals—few.
*Form.*—Broad based, hooked downward.
*Color.*—When young—brown.
*Position.*—Irregular.

Small prickles:

*Quantity.*—On main stalks—none. On laterals—none.

We claim:

1. A new and distinct variety of rose plant of the floribunda class, substantially as herein shown and described, characterized particularly as to novelty by the unique combination of its excellent year around production of cut flowers, Venetian pink bud and open flower, vigorous plant with large, dark Parsley green foliage.

No references cited.

ROBERT E. BAGWILL, Primary Examiner